(12) United States Patent
Woolfson et al.

(10) Patent No.: US 10,016,442 B2
(45) Date of Patent: *Jul. 10, 2018

(54) ESTROGEN COMPOSITIONS FOR VAGINAL ADMINISTRATION

(75) Inventors: David Woolfson, Belfast (IE); Karl Malcolm, Belfast (IE)

(73) Assignee: Allergan Pharmaceuticals International Limited, Dublin (IE)

( * ) Notice: Subject to any disclaimer, the term of this patent is extended or adjusted under 35 U.S.C. 154(b) by 1022 days.

This patent is subject to a terminal disclaimer.

(21) Appl. No.: 11/454,697

(22) Filed: Jun. 16, 2006

(65) Prior Publication Data

US 2007/0004694 A1    Jan. 4, 2007

Related U.S. Application Data

(60) Provisional application No. 60/691,442, filed on Jun. 16, 2005.

(51) Int. Cl.
| | | |
|---|---|---|
| *A61K 31/56* | (2006.01) | |
| *A61K 47/32* | (2006.01) | |
| *A61K 31/565* | (2006.01) | |
| *A61K 9/00* | (2006.01) | |
| *A61K 47/10* | (2017.01) | |

(52) U.S. Cl.
CPC .......... *A61K 31/565* (2013.01); *A61K 9/0034* (2013.01); *A61K 31/56* (2013.01); *A61K 47/10* (2013.01); *A61K 47/32* (2013.01)

(58) Field of Classification Search
CPC ...... A61K 31/56; A61K 47/32; A61K 9/0034; A61K 31/565; A61K 47/10
See application file for complete search history.

(56) References Cited

U.S. PATENT DOCUMENTS

| | | | | |
|---|---|---|---|---|
| 4,963,367 | A | * | 10/1990 | Ecanow .................... 424/485 |
| 5,242,951 | A | | 9/1993 | Akemi et al. |
| 5,349,030 | A | | 9/1994 | Long, II et al. |
| 5,514,673 | A | | 5/1996 | Heckenmuller et al. |
| 5,536,743 | A | | 7/1996 | Borgman |
| 5,543,150 | A | | 8/1996 | Bologna et al. |
| 5,741,525 | A | * | 4/1998 | Larsen ..................... 424/616 |
| 5,958,461 | A | * | 9/1999 | Larsen ..................... 424/614 |
| 6,060,077 | A | | 5/2000 | Meignant |
| 6,451,339 | B2 | | 9/2002 | Patel et al. |
| 7,067,504 | B2 | | 6/2006 | King et al. |
| 7,067,505 | B2 | | 6/2006 | King et al. |
| 2001/0036966 | A1 | | 11/2001 | Yasueda et al. |
| 2003/0175329 | A1 | | 9/2003 | Azarnoff et al. |
| 2003/0181430 | A1 | | 9/2003 | Gray et al. |
| 2003/0199426 | A1 | * | 10/2003 | Carrara et al. .................... 514/2 |
| 2004/0110732 | A1 | * | 6/2004 | Masini-Eteve et al. ...... 514/170 |
| 2005/0191338 | A1 | | 9/2005 | Kang et al. |
| 2005/0207990 | A1 | | 9/2005 | Funke et al. |
| 2006/0240111 | A1 | * | 10/2006 | Fernandez et al. ........... 424/487 |
| 2006/0292223 | A1 | | 12/2006 | Woolfson et al. |
| 2007/0004693 | A1 | | 1/2007 | Woolfson et al. |
| 2007/0004694 | A1 | | 1/2007 | Woolfson et al. |
| 2007/0015740 | A1 | | 1/2007 | Keown et al. |
| 2007/0015741 | A1 | | 1/2007 | Keown et al. |
| 2007/0036848 | A1 | | 2/2007 | Bortz et al. |
| 2007/0264349 | A1 | | 11/2007 | Lee et al. |
| 2009/0011019 | A1 | | 1/2009 | Jahagirdar et al. |
| 2009/0124584 | A1 | | 5/2009 | Lyle |

FOREIGN PATENT DOCUMENTS

| | | | |
|---|---|---|---|
| CN | 1198672 | 11/1998 | |
| DE | 19945522 A1 | 4/2001 | |
| EP | 0435200 A2 | 7/1991 | |
| EP | 0813412 | 12/1999 | |
| FR | 2739559 | * 4/1997 | .......... A61K 31/565 |
| WO | 9712618 A1 | 4/1997 | |
| WO | WO 97/12618 | * 4/1997 | .......... A61K 31/565 |
| WO | 2005007194 A1 | 1/2005 | |
| WO | 2005039531 A1 | 5/2005 | |
| WO | 2006/084082 A1 | 10/2006 | |

OTHER PUBLICATIONS

Saure et al, 1996. A randomized, double-blind, multicentra study comparing the clinical effects of two sequential estradiol-progestin combinations containing either desogestrel or norethisterone acetate in climacteric women with estrogen deficiency symptoms. Maturitas, vol. 24:111-118.*
Juang, Pharmaceutical Research, vol. 15, No. 11, p. 1714, 1998.*
Proniuk, Pharmaceutical Development and Technology, 7(2), 249, 2002.*
Rolf Daniels, Arzneiformen zur Hormontherapie, PZ Prisma, vol. 7, No. 1, pp. 42-52 (2000).
Elisabeth Amsellem, et al, In Vitro Studies on the Influence of Carbomers on the Availability and Acceptability of Estradiol Gels, Arzneim.-Forsch./Drug Res. 48(I), pp. 492-496 (1998).
Mohammad T. Islam, et al., "Fourier Transform Infrared Spectroscopy for the Analysis of Neutralizer-Carbomer and Surfactant-Carbomer Interactions in Aqueous, Hydroalcoholic, and Anhydrous Gel Formulations", The AAPS Journal, vol. 6, No. 4, Article 35, pp. 1-7 (2004).
Noveon. Product and Regulatory Guide: Bulletin 2, Carbopol and Viscosity, Jan. 2002, pp. 1-10.
"Flow and Suspension Properties of Carbopol® Polymers", Lubrizol Technical Data Sheet (TDS-180; Jan. 2002).
"Neutralizing Carbopol® and Pemulen™ Polymers in Aqueous and Hydroalcoholic Systems", Lubrizol Technical Data Sheet (TDS-237; Sep. 2009).
"Viscosity of Carbopol® Polymers in Aqueous Systems", Lubrizol Technical Data Sheet (TDS-730; Aug. 2010).

(Continued)

*Primary Examiner* — Matthew P Coughlin
*Assistant Examiner* — Thurman M Wheeler
(74) *Attorney, Agent, or Firm* — Fitzpatrick, Cella, Harper & Scinto

(57) ABSTRACT

Pharmaceutical gel compositions containing estrogen for vaginal administration, as well as a method of making the same, are disclosed.

22 Claims, 1 Drawing Sheet

(56) References Cited

OTHER PUBLICATIONS

"Dispersion Techniques for Lubrizol Pharmaceutical Polymers", Lubrizol Pharmaceutical Bulletin 4 (Oct. 2008).
"Thickening Properties", Lubrizol Pharmaceutical Bulletin 6 (Oct. 2008).
"Formulating Semisolid Products", Lubrizol Pharmaceutical Bulletin 21 (Aug. 2010).
"Carbopol® Polymers for Thickening, Suspending & Stabilizing", Lubrizol (CP-26; Sep. 2000).
"Carbopol® Aqua SF-1 Polymer Product", Lubrizol Product Summary Sheet (CP-29; Jun. 2006).
"Carbopol® Aqua SF-1 Polymer", Lubrizol Quick Start Guide (CP-29; Jun. 2006).
"Carbopol® Ultrez 20 Polymer", Lubrizol (CP-34; Jun. 2006).
"Pemulen™ Polymer Emulsifiers", Lubrizol (CP-26; Sep. 2000).
Carbopol® 846 "Synthetic Thickener for Textile Printing", Lubrizol (Jun. 2007).
Carbopol® EP-1 "High Efficiency Alkali Swellable Emulsion Thickener", Lubrizol (Jun. 2007).
Carbopol® EP-2 "Efficient Alkali Swellable Emulsion Thicker", Lubrizol (Jun. 2007).
Secundum Artem, Current and Practical Compounding Information for the Pharmacist, vol. 12, No. 3, available Feb. 8, 2004, pp. 1-10.
Drug Information Online, Drugs.com, revised Aug. 20, 1997, pp. 1-25.
Dubin, N.H., et al., "Prostaglandin Production by Rat Vaginal Tissue, in vitro, in Response to Ethanol, a Mild Mucosal Irritant", Toxicology and Applied Pharmacology, vol. 78, issue 3, May 1985, pp. 458-463.
Hydrogen Peroxide—Brighten Your Future with Us, Arkema (May 2005).
Abstract for JP 56087516 (Jul. 16, 1981).
Bulletin 8, BF Goodrich Polymers in Semisolid Products, May 1997.
Bulletin 11, BF Goodrich, Thickening Properties, May 1997.
Bulletin 14, BF Goodrich, Formulating Topical Products, May 1997.
TDS-43, Lubrizol, Carbopol Polymers Can Thicken Without Neutralization, Jan. 2002.

* cited by examiner

ESTROGEN COMPOSITIONS FOR VAGINAL ADMINISTRATION

This application claims the benefit of U.S. Provisional Patent Application No. 60/691,442, filed Jun. 16, 2005, the entire disclosure of which is incorporated by reference herein.

BACKGROUND OF THE INVENTION

Field of the Invention

This invention is directed to estrogen compositions for vaginal administration, as well as to methods of making and administering the same.

Related Background Art

Conventional semi-solid estrogen vaginal preparations comprise a two-phase emulsified system. Such conventional estrogen vaginal preparations have a significant hydrophobic oil or wax component, present either as the external or, more typically, the internal phase of a two-phase emulsified system, where water constitutes the other phase. Given the preferential solubility of estrogen in the hydrophobic phase, its availability for release into epithelial tissue upon vaginal application of such a preparation may be restricted.

Another problem encountered with conventional estrogen preparations for vaginal application is that they can be greasy and/or extremely difficult to remove completely from an applicator, particularly if the applicator is washed with water only.

The significant hydrophobic oil or wax component of conventional estrogen vaginal preparations contributes to both of these problems. Pharmaceutical gel compositions containing estrogen may be advantageous for vaginal use. As used herein, the term "gel" is understood to be a semi-solid matrix of particles interpenetrated by a liquid, in which the structural coherent matrix contains a high portion of liquid, usually an aqueous solvent such as water. Such gels comprise a single phase. As used herein, the term "semi-solid" is understood to refer to the rheological properties of the compositions themselves, such that the compositions will flow under an applied force but will remain in situ following application to the vaginal epithelial surface.

The inventors are not aware of any commercially available pharmaceutical gel compositions containing estrogen for vaginal administration. Known pharmaceutical gel compositions for topical administration conventionally comprise polymers, for example, modified cellulose ethers, natural gums or polymers containing pendant carboxylic acid groups, or their esters, or having pendant anhydrides of dicarboxylic acid groups, or mixtures thereof. Carboxylic acid polymers in aqueous systems are conventionally neutralized from a starting pH of about 2.5 to 3.5 to a pH of 4.0 or more in order to achieve gelation. Conventional neutralizers comprise sodium hydroxide, potassium hydroxide, ammonium hydroxide, arginine, aminomethyl propanol, tetrahydroxypropyl ethylenediamine, triethanolamine, tromethamine, PEG-15 cocamine, diisopropanolamine or triisopropanolamine. However, all polymer gel compositions, exemplified by the foregoing, will require the presence of an estrogen solubilizing agent to substantially solubilize the estrogen. For this reason, known pharmaceutical gel compositions for topical administration may conventionally contain an alcoholic component, ethanol, as an estrogen solubilizer.

More specifically, known pharmaceutical gel compositions for topical, but not for vaginal, application comprise Estrogel® (Solvay, US) and Sandrena® (Organon, Netherlands). Estrogel® is a hydro-ethanolic gel containing 0.06% estradiol; the excipients are ethanol, Carbomer 934 and triethanolamine, the balance being purified water. Sandrena® is another hydro-alcoholic gel containing 0.1% estradiol; its excipients are Carbomer 934, sodium hydroxide, propylene glycol, ethanol and water. Clearly, the base of these pharmaceutical gel compositions is a mixture of water and ethanol. The ethanol is intended to increase estrogen solubility in the gel and assist absorption into the stratum corneum. While the presence of ethanol may be useful in topical or skin formulations, its presence is counter-productive in mucosal utilities such as vaginal compositions since it is an irritant and it may also have a drying effect.

EP-B-435200 in the names of Nitto Denko Corp. and Teikoku Hormone Mfg. Co. relates to an estrogen-containing gel for topical, but not for vaginal, administration. The gels are covalently crosslinked using, for example, a titanium or aluminum chelate compound. There is no disclosure or suggestion that a gelation promoter might be selected to both solubilize the estrogen and to gel the polymer.

EP-B-813412 in the name of Laboratoire Innothera relates to vaginal gels containing estradiol in a gel containing a polymer that has been gelled by neutralization by a conventional neutralizer. There is no disclosure or suggestion that a gelation promoter might be selected to both solubilize the estrogen and to gel the polymer in a non-aqueous or substantially non-aqueous environment.

DE-A-199 45 522 in the name of Hexal AG relates to compositions for topical administration. The compositions are oil-in-water emulsions containing a polymer as a thickening agent. The compositions are erroneously described in DE-A-1 99 45 522 as gels. There is no disclosure or suggestion that a gelation promoter might be selected to both solubilize the estrogen and to gel the polymer.

Accordingly, pharmaceutical gel compositions containing estrogen for vaginal administration which do not suffer from the deficiencies of conventional vaginal preparations and topical gel compositions are highly desirable.

SUMMARY OF THE INVENTION

The present invention is directed to a pharmaceutical gel composition containing estrogen for vaginal administration comprising (a) at least one estrogen in an amount of about 0.00001% to about 2% by weight of the composition; (b) at least one hydrogen-bonding gelation polymer; and (c) at least one gelation promoter in an amount effective to substantially solubilize the estrogen and to gel the polymer, wherein at least a portion of the estrogen is dissolved in the composition at 15° C. The formation of a gel from one or more suitable hydrogen-bonding gelation polymer(s) capable of viscosity enhancement in the presence of at least one gelation promoter capable of both causing gelation promotion and substantial solubilization of the at least one estrogen is desirable for both improved release rate of the drug from the product and for a more elegant water-washable product. In preferred embodiments, the hydrogen-bonding gelation polymer is present in an amount sufficient to form a gel with a viscosity ranging from about 50 Pa·s to about 1000 Pa·s at 20° C. In other preferred embodiments, at least 50%, more preferably at least 60%, and most preferably at least 90% of the estrogen is dissolved at 15° C.

In certain embodiments of the present invention, the at least one estrogen is 17β-estradiol, mestranol, conjugated estrogens USP, estrone, or ethinyl estradiol or salts, esters or prodrugs thereof. In certain embodiments, the at least one hydrogen-bonding gelation polymer is a homopolymer, copolymer or interpolymer having pendant carboxylic acid groups, having pendant anhydrides of dicarboxylic acid groups, or having both (or esters of any thereof). In certain embodiments, the at least one gelation promoter is at least one polyhydric alcohol, at least one polyglycol or a combination thereof. In certain embodiments, the gelation promoter comprises an aqueous solution of a gelation promoter.

The present invention is further directed to a method of making pharmaceutical gel compositions containing estrogen for vaginal administration comprising the step of admixing at least one estrogen in an amount of about 0.00001% to about 2% by weight of the composition, at least one gelation promoter or aqueous solution thereof in an amount effective to substantially solubilize the estrogen and to gel the polymer, and at least one hydrogen-bonding gelation polymer to form the pharmaceutical gel composition, wherein at least a portion of the estrogen is dissolved in the composition at 15° C. In a preferred embodiment, the admixing comprises (a) solubilizing the estrogen in the gelation promoter (or in the aqueous solution of the gelation promoter) to form a substantially solubilized estrogen preparation; and (b) combining the substantially solubilized estrogen preparation with the hydrogen-bonding gelation polymer to form the pharmaceutical gel composition.

The present invention is still further directed to a pharmaceutical gel composition made according to the present inventive method and to a method of administering the pharmaceutical gel composition of the present invention.

DETAILED DESCRIPTION OF THE INVENTION

Figure 1:
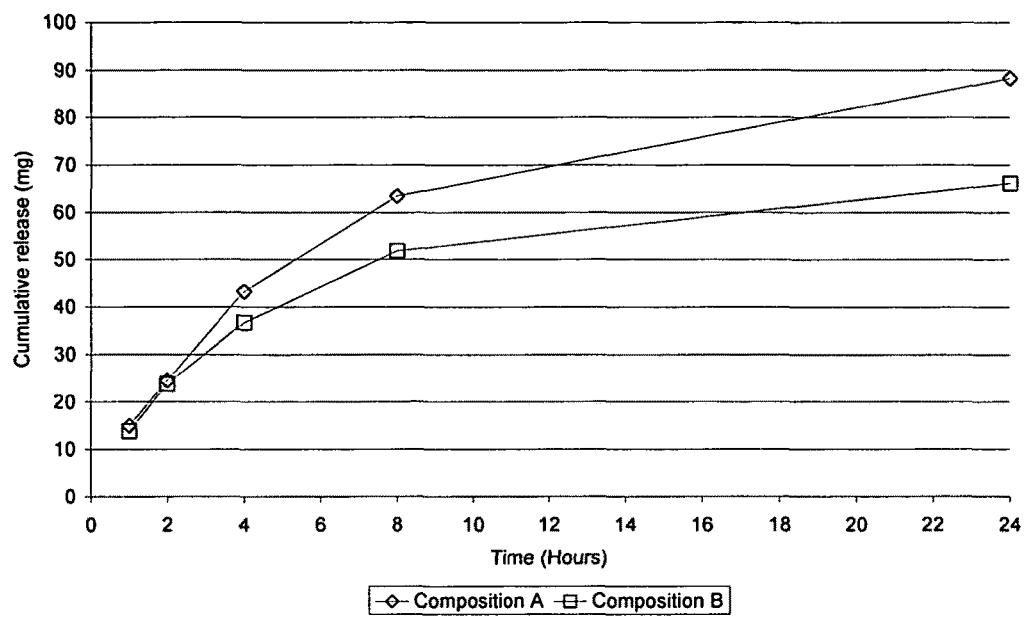
FIG. 1 illustrates the cumulative drug release of both an emulsified oil in water preparation and a pharmaceutical gel composition containing solubilized estrogen for vaginal administration of the present invention.

Without being bound by theory, as used herein, "hydrogen-bonding gelation polymer" refers to polymers, which are capable of taking part in hydrogen bonding with the functional groups of a gelation promoter. Such polymers may also be capable of gelation by neutralization but, in the compositions of the present invention, gelation is achieved by hydrogen-bonding. As used herein, "hydrogen-bonding" refers to a non-covalent bond between hydrogen and another atom, usually nitrogen or oxygen. Hydrogen bonding does not involve the sharing of electrons between the bonded atoms and, therefore, does not satisfy the valence of either atom.

As used herein, "gelation promoter" refers to a substance having at least two functional groups which, it is thought, can take part in hydrogen bonding with a gelation polymer to accomplish uncoiling and/or cross-linking of a polymer chain and also acts as a solubilizer of estrogen. Such functional groups comprise hydroxy or ethoxy (defined as —O— or ether links) groups, or a mixture thereof. The term "gelation promoter" excludes any substance having a single functional group, which could possibly take part in hydrogen-bonding. Such excluded substances include ethanol.

The first embodiment of the present invention is a pharmaceutical gel formulation containing estrogen for vaginal administration comprising at least one substantially solubilized estrogen, at least one hydrogen-bonding gelation polymer, and at least one gelation promoter. As used herein, "substantially solubilized" refers to at least a portion of the estrogen being dissolved; more specifically, it refers to at least 50% of the estrogen, more preferably at least 60%, and most preferably at least 90%, of the estrogen being dissolved at 15° C. The units % relate to % w/w, so that "at least 50%" requires that at least half, by weight, of the added estrogen is dissolved in the composition at 15° C. For purposes of any of the first to fourth embodiments of this invention, it is to be understood that "dissolved" can refer to either or both of dissolution in the composition as a whole or dissolution in the gelation promoter or an aqueous solution of the gelation promoter.

An exemplary method of measuring the proportion of the estrogen dissolved in the composition at 15° C. is based on the solubility of the estrogen in the gelation promoter at 15° C. The solubility of the estrogen in the gelation promoter (or an aqueous solution thereof) at 15° C. is calculated by preparing saturated solutions of the estrogen in the gelation promoter at 15° C. (in triplicate). These saturated solutions were prepared by adding the estrogen to the gelation promoter at 15° C. until saturation was achieved (i.e., no more estrogen dissolved in the gelation promoter). The saturated solutions were then placed in a shaker at 15° C. for 12 hours, after which time more estrogen was added if required. Finally, the saturated solutions were centrifuged at 15° C. and the supernatant analyzed by HPLC to determine the amount of dissolved estrogen in the gelation promoter or an aqueous solution thereof. The solubility of the estrogen in the composition is measured by first centrifuging the composition under centrifugation conditions sufficient to remove any suspended estrogen, and then extracting the estrogen from the supernatant using a suitable solvent (such as ethanol) or solvent mixture. The solvent extract is then analyzed by HPLC to determine the amount of dissolved estrogen in the composition at 15° C.

Suitable forms of estrogen include, without limitation, 17β-estradiol, mestranol, conjugated estrogens USP, estrone, ethinyl estradiol, and combinations thereof, as well as salts, esters or prodrugs of any thereof. Other suitable estrogens include those described in each of U.S. patent application Ser. Nos. 11/009,617 and 11/009,618, each filed on Dec. 10, 2004, and those described in each of U.S. Provisional Patent Application Nos. 60/698,865 and 60/698,866, each filed on Jul. 12, 2005. The disclosures of each of these applications are incorporated in their entirety by reference herein. The estrogen is included in the pharmaceutical composition of the present invention in an amount ranging from about 0.00001% to about 2%, more preferably from about 0.0005% to about 0.05%, still more preferably from about 0.00075% to about 0.025%, by weight of the composition.

Hydrogen-bonding gelation polymers suitable for use in the present invention include, without limitation, homopolymers, copolymers and interpolymers having pendant carboxylic acid groups and/or having pendant anhydrides of dicarboxylic acid groups, or esters of any thereof, such as polyacrylic acid derivatives or copolymers of acrylic acid with long-chain alkyl acrylates (e.g., those sold under the tradename Carbopol® (Noveon, US)) or polymethyl vinyl ether/maleic anhydride copolymers (e.g., those commercially available under the tradename Gantrez® (ISP, US)) and combinations thereof. The hydrogen-bonding gelation polymer may be cross-linked or not. While acrylic acid is the most common primary monomer, other suitable monomers include all α-β unsaturated monomers with carboxylic pendant groups or anhydrides of dicarboxylic acids (see, U.S. Pat. No. 5,349,030, the contents of which are incorporated herein by reference).

The pharmaceutical gel compositions of the present invention may contain, as the hydrogen-bonding gelation polymer, at least one poly(acrylic) acid (carbomer) or a mixture thereof. Lightly crosslinked poly(acrylic) acid polymers, commercially available in a range of viscosities as Carbopol® are suitable. Poly(acrylic) acid polymers with a greater degree of crosslinking, commercially available as Noveon® are also suitable. Mixtures of the aforementioned polymers are also suitable. Carbopol® polymers are preferred. While it will be apparent that many such polymers may be employed in the present invention, Carbopol® polymers with a Brookfield viscosity (measured at 25° C. at 20 rpm using 0.5% (w/w) aqueous solution) of between 3,000 and 15,000 cP are preferred—suitable examples are Carbopol® 941NF, Carbopol® 981NF, Carbopol® 971NF and Carbopol® ETD2050. Carbopol® 974P is most preferred.

The hydrogen-bonding gelation polymer is included in the pharmaceutical gel composition in an amount to give a viscosity of between about 50 Pa·s and about 1000 Pa·s at 20° C., more preferably between about 80 Pa·s and about 300 Pa·s at 20° C.

The gelation promoter of the present invention, in theory, aids in gel formation by uncoiling polymer chains by supplying functional groups (hydroxyl groups or ether links) which are capable of participating in hydrogen bonding with the carboxylic acid groups on the backbone of the hydrogen-bonding gelation polymer. Without being bound by theory, gelation is subsequently thought to occur via linear chain entanglement or cross-linking, depending on the nature of the gelation polymers. According to the present invention, the gelation promoter must have at least two functional groups capable of participating in hydrogen bonding with the hydrogen-bonding gelation polymer. Suitable gelation promoters therefore include, without limitation, polyhydric alcohols, polyglycols, and combinations thereof. Preferred gelation promoters include glycerol, propylene glycol and low molecular weight polyethylene glycols which remain as liquids as room temperature, i.e., polyethylene glycol 200 to 700, for example, polyethylene glycol 400.

Exemplary polyhydric alcohols include, without limitation, 1,2-butanediol, 1,3-butanediol, 1,4-butanediol, butynediol, butenediol, diethylene glycol, ethylene glycol, glycerol, glycofurol, 1,2-hexanediol, 1,2,6-hexanetriol, 3-methyl-1,5-pentanediol, 2-methyl-1,3-propanediol, 1,9-nonanediol, 1,5-pentanediol, poly(vinyl alcohol), 1,3-propanediol and propylene glycol. In addition, solutions of solid polyhydric alcohols could be used.

Exemplary polyglycols include, without limitation, butyl glycol, butyl diglycol, butyl polyglycol, diethylene glycol monomethyl ether, diethylene glycol dimethyl ether, diethylene glycol monoethyl ether, diethylene glycol diethyl ether, dipropylene glycol, dipropylene glycol dimethyl ether, poloxamers, methyl diglycol, methyl triglycol, methyl tetraglycol, poly(ethylene glycol), poly(oxyethylene) alkyl ethers, poly(oxyethylene) alkyl esters, poly(propylene glycol), tetraethylene glycol dimethyl ether, triethylene glycol, triethyl glycol dimethyl ether, tripropylene glycol, and glycol-silane copolymers. In certain preferred embodiments, the gelation promoter is polyethylene glycol. In other preferred embodiments, the gelation promoter is a poloxamer, i.e., a copolymer of polyoxyethylene and polyoxypropylene. In other preferred embodiments, the gelation promoter is selected from the group comprising propylene glycol, polyethylene glycol (such as PEG 400) and glycerol.

The at least one gelation promoter is present in the pharmaceutical gel composition of the present invention in an amount effective to gel the hydrogen-bonding gelation polymer and to substantially solubilize the estrogen. The gelation promoter may comprise one of the materials noted above or an aqueous solution of one of the materials noted above, or a mixture thereof. When the gelation promoter is incorporated as an aqueous solution, the aqueous solvent may be water (most preferred) or some combination of water and water-miscible solvents.

In view of the importance of avoiding conventional estrogen solubilizing agents in the pharmaceutical gel compositions of the present invention, the pharmaceutical compositions are substantially free of estrogen solubilizing agents such as ethanol. As used herein, the term "substantially free" is understood to be less than about 0.05% of said estrogen solubilizing agent, preferably less than about 0.005% of said estrogen solubilizing agent, still more preferably less than about 0.001% of said estrogen solubilizing agent, by weight of the composition. In a particular embodiment, the term "substantially free" may be understood to be less than about 0.05% of ethanol, preferably less than about 0.005% of ethanol, still more preferably less than about 0.001% of ethanol, by weight of the composition. All % units are w/w.

Without wishing to be bound by theory, it is believed that the hydrogen-bonding gelation polymer forms hydrogen bonds with the gelation promoter, resulting in thickening of the matrix without resorting to conventional neutralizers. The gel matrix so achieved is a clear or almost clear, transparent matrix. This is desirable from the user's point of view. The gel matrix so achieved is, in itself, bioadhesive, more specifically mucoadhesive, in that the gel matrix possesses the property of being able to persist at a vaginal epithelial surface by, it is believed, polymer entanglement with surface mucin and/or non-covalent bond formation between the polymer(s) of the gel matrix and surface mucin. This is desirable for vaginal epithelial delivery.

The pharmaceutical gel compositions of the present invention may also contain other suitable active ingredients. Suitable active ingredients include, without limitation, other steroids such as a progestogen (for example, progestogen and its derivatives such as 17-hydroxy progestogen esters and 19-nor-17-hydroxy progestogen esters, norgestrel, norgestimate, demegestone, drospirenone, dydrogesterone, medrogestone, medroxy progesterone and esters thereof such as medroxy progesterone acetate, norethesterone, norethindrone, norethindrone acetate, levonorgestrel, desogestrel, 3-ketodesogestrel, gestodene and the like) or an androgen (such as testosterone, esters thereof, methyl-testosterone and prodrugs and combinations thereof), in an amount appropriate for clinical efficacy.

The pharmaceutical composition of the present invention may also contain any pharmaceutically acceptable excipient, as desired. When present, such pharmaceutically acceptable excipients are included in an amount which can be readily determined by one of ordinary skill in the art. Suitable excipients include, without limitation, poly(vinyl alcohol), hydroxyethylcellulose, hydroxypropylcellulose, hydroxypropylmethylcellulose, waxes (such as white soft paraffin), suitable preservatives including, without limitation, para-hydroxy benzoate compounds, buffers (for example, those buffers comprising weak organic acids such as lactic acid or acetic acid) and combinations thereof.

The second embodiment comprises a method of making a pharmaceutical gel composition containing estrogen for vaginal administration comprising the step of admixing at least one estrogen in an amount of about 0.00001% to about 2% by weight of the composition, at least one gelation promoter or aqueous solution thereof in an amount effective to substantially solubilize the estrogen and to gel the polymer, and at least one hydrogen-bonding gelation polymer to form the pharmaceutical gel composition, wherein at least a portion of the estrogen is dissolved in the composition at 15° C. The ingredients can be admixed using any suitable means. Typically, any mixing step is accomplished in a suitable vessel with vigorous agitation, i.e., high shear mixing. According to a preferred embodiment of the inventive method, the admixing is accomplished by substantially solubilizing the estrogen in the gelation promoter (or aqueous solution thereof) to form a substantially solubilized estrogen preparation and then combining the substantially solubilized estrogen preparation with the hydrogen-bonding gelation polymer to form the pharmaceutical gel composition.

Optional additional steps include those which result in the addition of one or more of another active ingredient(s), pharmaceutically acceptable excipient(s) and preservative(s). The details regarding the estrogen, hydrogen-bonding gelation polymer and gelation promoter, i.e., type and amount, as well as the details regarding other possible ingredients, are as set forth above with regard to the first embodiment of this invention.

An additional embodiment of the present invention is directed to a pharmaceutical gel composition made according to the method of the second embodiment of the invention.

Still another embodiment of the present invention is directed to a method of vaginal administration of estrogen for a female comprising the step of administering the pharmaceutical gel composition of the present invention to the vaginal epithelial tissue of the female.

Specific embodiments of the invention will now be demonstrated by reference to the following examples. It should be understood that these examples are disclosed solely by way of illustrating the invention and should not be taken in any way to limit the scope of the present invention.

Example 1

Anhydrous Gelation Promoter/Carbomer/Estradiol Formulation

A single-phase pharmaceutical gel composition was made to contain the components set forth in Table 1 below.

TABLE 1

| Ingredient | % w/w |
| --- | --- |
| Carbomer (Carbopol 974P) | 2.50 |
| propylene glycol | 97.49 |
| 17β-estradiol | 0.01 |

Estradiol was added to an aliquot of the propylene glycol. Dissolution of the estradiol in propylene glycol was achieved by high shear mixing using a suitable mixer.

The rest of the propylene glycol was dispensed into a vacuum rated mixing vessel to which the estradiol stock solution is added. The Carbomer polymer was added to the vortex created by rapid mixing of the estradiol and propylene glycol solution. Rapid mixing (~3000 rpm) was achieved using a suitable high shear mixer. Dispersion of the polymer was achieved in approximately 15 minutes. Following the dispersion, the system existed in a fluid state, and to prevent sedimentation of the dispersed polymer, the system was mixed using a planetary mixer at ~20 rpm. After approximately 60 minutes, the system began to gel, the planetary mixer was halted and a vacuum was drawn. Following deaeration, samples were withdrawn for in-process testing. This testing consisted of determining the assay value for the estradiol in the stock solution and the content uniformity in the gel mixture. Results of this testing can be seen in Table 2.

TABLE 2

| Test | Limits<br>% w/w estradiol | Results<br>% w/w estradiol |
| --- | --- | --- |
| Stock assay | 1.9–2.1 | 1.984 |
| Content Uniformity | Between 0.0090–0.0110 | 0.0098* |

*average of seven samples

The gel mix was then transferred to filling equipment. Aluminum tubes were filled with a specified weight of gel. The pressure required to fill the tubes was approximately 2 bar. The tubes were then crimped in a triple fold. The gel was tested against a defined specification. The results of this testing can be seen in Table 3.

TABLE 3

| Test | Limits | Result |
| --- | --- | --- |
| APPEARANCE | Clear gel that is free from foreign matter | Complies |
| TOTAL DRUG ASSAY | Between 0.0090–0.0110% w/w Record all results (% w/w) | 0.0098% |
| RELATED SUBSTANCES | Each individual unknown not more than 1.0%: record result | Highest = 0.14% |
|  | Total of all related substances not more than 5.0%: record result | Total = 0.36% |

As can be seen, the gel produced complied with all specification limits. The solubility of estradiol in propylene glycol as measured by the method set forth above is 20 mg/ml at 15° C. Therefore in this example, 100% of the estradiol is dissolved in the composition at 15° C.

The gel viscosity was determined using a TA Advanced Rheometer AR550 in stepped flow mode, with a time constant of 10 seconds. The sample was loaded between a set of 40 mm standard parallel plates, with a plate gap of 1000 microns. The sample was allowed to equilibrate for 2 minutes before the shear stress was applied. A fresh sample was applied for each replicate analysis. The shear stress was increased from 100-300 Pa, and the viscosity was determined by application of the Power Law Model to the resulting flow rheogram. All analyses were performed at a controlled temperature of 20° C. Three readings were performed, and an average viscosity calculated. Using this method, a viscosity of 137 Pa·s at 20° C. was obtained for the pharmaceutical gel composition of Example 1.

Example 2

Anhydrous Gelation Promoter/Carbomer/Estradiol Formulation

A single-phase pharmaceutical gel composition was made to contain the components set forth in Table 4 below.

TABLE 4

| Ingredient | % w/w |
| --- | --- |
| Carbomer (Carbopol 974P) | 2.000 |
| propylene glycol | 97.998 |
| 17β-estradiol | 0.0015 |

The 17β-estradiol was solubilized in a stock solution of propylene glycol and then added to the remainder of the propylene glycol. Then, the carbomer was added and mixed with high shear until gelation occurred. A pharmaceutical gel composition having a viscosity of 130 Pa·s at 20° C. was obtained (as determined using the method of Example 1). In this example, 100% of the estradiol is dissolved in the composition at 15° C.

Example 3

Mixed Gelation Promoter/Carbomer/Estradiol Composition

A single phase pharmaceutical gel composition was made to contain the components set forth in Table 5 below.

TABLE 5

| Ingredient | % w/w |
| --- | --- |
| carbomer (Carbopol 974P) | 2.50 |
| propylene glycol | 77.29 |
| water (qs) | to 100% |
| 17β-estradiol | 0.01 |
| Nipaseptsodium | 0.20 |

The 17β-estradiol was solubilized in a stock solution of propylene glycol at 20° C. and then added to the remainder of the propylene glycol and the water. The Nipasept sodium, functioning as an antimicrobial preservative, was then added and stirred. Then, the carbomer was added and mixed with high shear until gelation occurred. A pharmaceutical gel composition having a viscosity of 164 Pa·s at 20° C. was obtained, using the method as in Example 1. In this example, 100% of the estradiol is dissolved in the composition at 15° C.

Example 4

Mixed Gelation Promoter/Carbomer/Estradiol Composition

A single phase pharmaceutical gel composition was made to contain the components set forth in Table 6 below.

TABLE 6

| Ingredient | % w/w |
| --- | --- |
| carbomer (Carbopol 974P) | 2.50 |
| propylene glycol | 49.34 |
| water (qs) | to 100% |
| 17β-estradiol | 0.00015 |
| Methylparaben | 0.08 |
| Propylparaben | 0.02 |

The 17β-estradiol was solubilized in a stock solution of propylene glycol at 20° C. and then added to the remainder of the propylene glycol and the water. The methyl and propyl parabens, functioning as antimicrobial preservatives, were then added and stirred. Then, the carbomer was added and mixed with high shear until gelation occurred. A pharmaceutical gel composition having a viscosity of 148 Pa·s at 20° C. was obtained (as determined using the method of Example 1). In this example, 100% of the estradiol is dissolved in the composition at 15° C.

Example 5

Mixed Gelation Promoter/Carbomer/Estradiol Composition

A single phase pharmaceutical gel composition was made to contain the components set forth in Table 7 below.

TABLE 7

| Ingredient | % w/w |
| --- | --- |
| carbomer (Carbopol 974P) | 2.00 |
| propylene glycol | 46.40 |
| water (qs) | to 100% |
| 17β-estradiol | 0.0015 |
| Methylparaben | 0.08 |
| Propylparaben | 0.02 |

The 17β-estradiol was solubilized in a stock solution of propylene glycol at 20° C. and then added to the remainder of the propylene glycol and the water. The methyl and propyl parabens, functioning as antimicrobial preservatives, were then added and stirred. Then, the carbomer was added and mixed with high shear until gelation occurred. A pharmaceutical gel composition having a viscosity of 61 Pa·s at 20° C. was obtained (as determined using the method of Example 1). In this example, 100% of the estradiol is dissolved in the composition at 15° C.

Example 6

Mixed Gelation Promoter/Carbomer/Estradiol Composition

A single phase pharmaceutical gel composition was made to contain the components set forth in Table 8 below.

TABLE 8

| Ingredient | % w/w |
| --- | --- |
| carbomer (Carbopol 974P) | 2.50 |
| Propylene glycol | 77.2985 |
| water (qs) | to 100% |
| 17β-estradiol | 0.0015 |
| Nipaseptsodium | 0.20 |

The 17β-estradiol was solubilized in a stock solution of propylene glycol at 20° C. and then added to the remainder of the propylene glycol and the water. The Nipasept sodium, functioning as an antimicrobial preservative, was then added and stirred. Then, the carbomer was added and mixed with high shear until gelation occurred. A pharmaceutical gel composition having a viscosity of 157 Pa·s at 20° C. was obtained (as determined using the method of Example 1). In this example, 100% of the estradiol is dissolved in the composition at 15° C.

Example 7

Anhydrous Gelation Promoter/Carbomer/Estradiol Formulation

A single-phase gelled pharmaceutical composition was made to contain the components set forth in Table 9 below.

TABLE 9

| Ingredient | % w/w |
|---|---|
| Carbomer (Carbopol 974P) | 2.50 |
| Glycerol | 97.49 |
| 17β-estradiol | 0.01 |

The 17β-estradiol was solubilized in a stock solution of glycerol and then added to the remainder of glycerol. Then, the carbomer was added and mixed with high shear until gelation occurred. A pharmaceutical gel composition having a viscosity of 731 Pa·s at 20° C. was obtained (as determined using the method of Example 1, except that the shear stress was increased from 300 to 700 Pa).

Example 8

Anhydrous Gelation Promoter/Carbomer/Estradiol Formulation

A single-phase pharmaceutical gel composition was made to contain the components set forth in Table 10 below.

TABLE 10

| Ingredient | % w/w |
|---|---|
| carbomer (Carbopol 974P) | 2.50 |
| Polyethylene glycol-400 | 97.49 |
| 17β-estradiol | 0.01 |

The 17β-estradiol was solubilized in a stock solution of polyethylene glycol-400 and then added to the remainder of the polyethylene glycol-400. Then, the carbomer was added and mixed with high shear until gelation occurred. A pharmaceutical gel composition having a viscosity of 71 Pa·s at 20° C. was obtained (as determined using the method of Example 1).

Example 9

Anhydrous Gelation Promoter/Carbomer Formulation

A single-phase pharmaceutical gel composition was made to contain the components set forth in Table 11 below.

TABLE 11

| Ingredient | % w/w |
|---|---|
| carbomer (Carbopol 974P) | 2.50 |
| Ethylene glycol | 97.49 |
| 17β-estradiol | 0.01 |

The 17β-estradiol was solubilized in a stock of ethylene glycol and then added to the remainder of the ethylene glycol. Then the carbomer was added and mixed with high shear until gelation occurred. A pharmaceutical gel composition having a viscosity of 193.4 Pa·s at 20° C. was obtained (as determined using the method of Example 1, except that the shear stress was increased from 50 to 250 Pa).

Stability Testing

The stability of the pharmaceutical gel composition of Example 2 was evaluated over the course of 15 months under the storage conditions of 40° C.±2° C. and 75%±5% relative humidity. The composition was assessed in a 16×70 mm aluminum tube with membrane (internal lacquer IT 404) maintained at the storage conditions specified. The composition was analyzed at 0 months, 1 month, 6 months and 15 months for both active ingredient (estradiol) content and total related substance content. The results of the evaluation are set forth in Table 12 below.

TABLE 12

| Time (months) | Estradiol content (%) | Total Related substance content (%) |
|---|---|---|
| 0 | 94.00 | 0.15 |
| 1 | 95.90 | 0.53 |
| 6 | 95.70 | 0.92 |
| 15 | 96.90 | 1.31 |

As can be seen from the results, after fifteen months under these storage conditions, the assay value for the gel does not change significantly and is still well within the specification limit of 90% to 110% of label claim.

Comparative Release Studies

Two different 17β-estradiol vaginal compositions were made for studying comparative release of active ingredient—Composition A, a pharmaceutical gel according to the present invention, and Composition B, a conventional oil-in-water cream.

TABLE 13

| Composition | Dispersion medium | % (w/w) | Carbopol 971PNF % w/w | E2 % w/w |
|---|---|---|---|---|
| B | Aqueous cream | 98.00 | — | 2.00 |
| A | Propylene Glycol | 96.00 | 2.00 | 2.00 |

Composition A was made by dispersing the desired quantity of 17β-estradiol (E2) in 96.00 g propylene glycol. The mixture was stirred slowly and 2.00 g of poly (acrylic) acid (Carbopol® 971PNF) was slowly sifted into the vortex with continuous stirring at 300 rpm (Heidolph mixer with flat blade propeller). High shear mixing was continued until no polymer aggregates were visible. Stirring was continued for 15 minutes at room temperature until a semi-solid gel state was achieved. The resulting product was passed through a laboratory homogenizer and centrifuged at 3000 rpm for 15 minutes to remove entrapped air. The product was packaged in 25 g aliquots into lacquered ointment tubes.

In a similar manner, Composition B was made by adding the desired quantity of 17β-estradiol (E2) to a pre-formed oil-in-water cream (Aqueous Cream BP) system. The composition was mixed, allowing sufficient time (10 minutes) for the 17β-estradiol to disperse into the dispersion medium. Composition B was not centrifuged due to the risk of separation of the oil-in-water emulsion.

Compositions A and B were tested for their comparative drug release properties as follows: 5.00 g of the test composition (A or B, respectively) was placed in a modified perforated cellulose bag, which was then sealed with tape. The bag was then positioned in 100 ml of 1% w/w benzalkonium chloride solution at 37° C. and placed in an orbital shaking incubator (Gallenkamp IOC, 37° C., 60 RPM). Samples were taken from the benzalkonium chloride solution at 1 hour, 4 hours and 24 hours and analyzed by high-performance liquid chromatography (HPLC) using the following method:

column: Symmetry Shield™ RP18 5 μm 4.6×150 mm
   mobile phase: 50:50 Acetonitrile:pH 2.5 phosphate buffer
   flow rate: 0.8 mL/min
   injection volume: 20 μl
   wavelength: 225 nm
   column temperature: 30° C.

Figure 2:
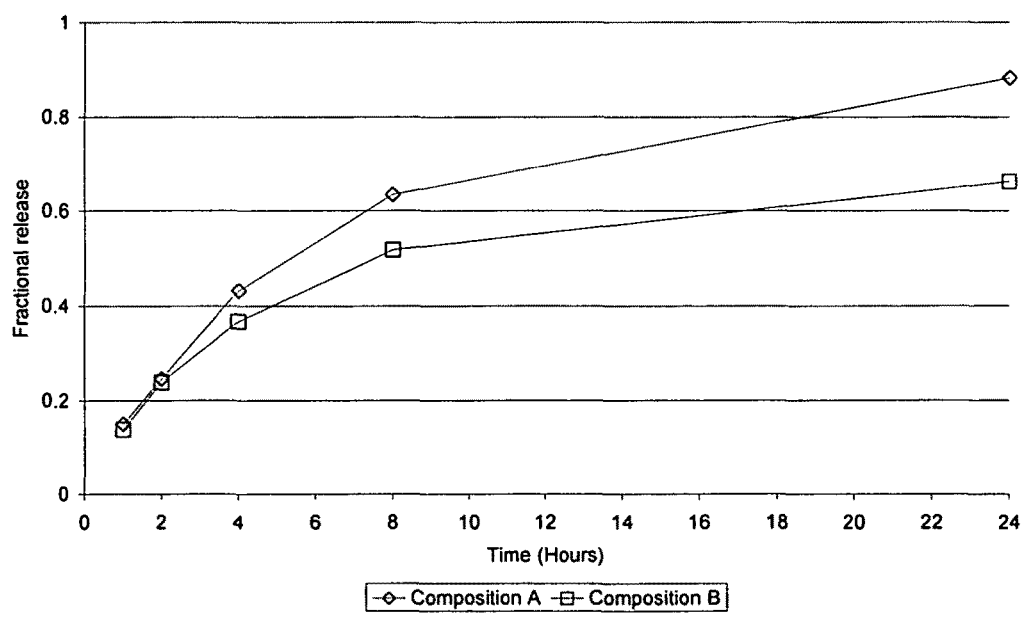
FIG. 2 illustrates the fractional drug release of both an emulsified oil in water preparation and a pharmaceutical gel composition containing solubilized estrogen for vaginal administration of the present invention.

The results are presented in FIG. 1 (cumulative release) and FIG. 2 (fractional release) of the accompanying drawings. The pharmaceutical gel Composition A showed an approximately 33% greater release after 24 hours when compared with a conventional oil-in-water cream formulation (Composition B).

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A pharmaceutical composition for vaginal administration consisting of:
   (a) at least one estrogen selected from 17β-estradiol or salt thereof in an amount of about 0.00001% to about 2% by weight of the composition;
   (b) at least one hydrogen-bonding gelation polymer that is a homopolymer, copolymer or interpolymer of acrylic acid; and
   (c) at least one gelation promoter selected from the group consisting of polyhydric alcohols, polyglycols and combinations thereof in an amount effective to gel said polymer and to substantially solubilize the estrogen,
   wherein at least 50% of the estrogen is dissolved in said composition at 15° C., and
   wherein said composition is substantially free of ethanol.

2. The pharmaceutical composition of claim 1, wherein the at least one estrogen is 17β-estradiol.

3. The pharmaceutical composition of claim 1, wherein the amount of the at least one estrogen is from about 0.0005% to about 0.05% by weight of the composition.

4. The pharmaceutical composition of claim 3, wherein the amount of the at least one estrogen is from about 0.00075% to about 0.025% by weight of the composition.

5. The pharmaceutical composition of claim 1, wherein the at least one hydrogen-bonding gelation polymer is present in an amount sufficient to form a gel with a viscosity ranging from about 50 Pa·s to about 1000 Pa·s at 20° C.

6. A pharmaceutical composition for vaginal administration consisting of:
   (a) at least one estrogen selected from 17β-estradiol or salt thereof in an amount of about 0.00001% to about 2% by weight of the composition;
   (b) at least one hydrogen-bonding gelation polymer that is a homopolymer, copolymer or interpolymer of acrylic acid;
   (c) at least one gelation promoter selected from the group consisting of polyhydric alcohols, polyglycols and combinations thereof in an amount effective to gel said polymer and to substantially solubilize the estrogen; and
   (d) water,
   wherein at least 50% of the estrogen is dissolved in said composition at 15° C., and
   wherein said composition is substantially free of ethanol.

7. The pharmaceutical composition of claim 1, wherein the polyhydric alcohol is selected from the group consisting of 1,2-butanediol, 1,3-butanediol, 1,4-butanediol, butynediol, butenediol, diethylene glycol, ethylene glycol, glycerol, glycofurol, 1,2-hexanediol, 1,2,6-hexanetriol, 3-methyl-1,5-pentanediol, 2-methyl-1,3-propanediol, 1,9-nonanediol, 1,5-pentanediol, poly(vinyl alcohol), 1,3-propanediol, propylene glycol and combinations thereof.

8. The pharmaceutical composition of claim 1, wherein the polyglycol is selected from the group consisting of butyl glycol, butyl diglycol, butyl polyglycol, diethylene glycol monomethyl ether, diethylene glycol dimethyl ether, diethylene glycol monoethyl ether, diethylene glycol diethyl ether, dipropylene glycol, dipropylene glycol dimethyl ether, poloxamers, methyl diglycol, methyl triglycol, methyl tetraglycol, poly(ethylene glycol), poly(oxyethylene) alkyl ethers, poly(oxyethylene) alkyl esters, poly(propylene glycol), tetraethylene glycol dimethyl ether, triethylene glycol, triethyl glycol dimethyl ether, tripropylene glycol, glycol-silane copolymers and combinations thereof.

9. The pharmaceutical composition of claim 1, wherein the polyglycol is selected from the group consisting of polyoxyethylene, polyoxypropylene, a copolymer of polyoxyethylene and polyoxypropylene and combinations thereof.

10. The pharmaceutical composition of claim 1, wherein at least 60% of the estrogen is dissolved in said composition at 15° C.

11. The pharmaceutical composition of claim 10, wherein at least 90% of the estrogen is dissolved in said composition at 15° C.

12. A method of making a pharmaceutical composition for vaginal administration consisting of the step of admixing at least one estrogen selected from 17β-estradiol or salt thereof in an amount of about 0.00001% to about 2% by weight of the composition, at least one hydrogen-bonding gelation polymer that is a homopolymer, copolymer or interpolymer of acrylic acid, and at least one gelation promoter, the gelation promoter being selected from the group consisting of polyhydric alcohols, polyglycols and combinations thereof in an amount effective to substantially solubilize the estrogen and to gel the polymer to form the pharmaceutical composition, wherein at least 50% of the estrogen is dissolved in the composition at 15° C., and wherein said composition is substantially free of ethanol.

13. The method of claim 12, wherein the admixing step consists of (a) substantially solubilizing the estrogen in the gelation promoter or in an aqueous solution thereof to form a substantially solubilized estrogen preparation and (b) combining the substantially solubilized estrogen preparation with the hydrogen-bonding gelation polymer to form the pharmaceutical composition.

14. A pharmaceutical composition made by the step of admixing at least one estrogen selected from 17β-estradiol or salt thereof in an amount of about 0.00001% to about 2% by weight of the composition, at least one hydrogen-bonding gelation polymer that is a homopolymer, copolymer or interpolymer of acrylic acid, and at least one gelation promoter, the gelation promoter being selected from the group consisting of polyhydric alcohols, polyglycols and combinations thereof in an amount effective to substantially solubilize the estrogen and to gel the polymer to form the pharmaceutical composition, wherein at least 50% of the estrogen is dissolved in the composition at 15° C., wherein said composition is substantially free of ethanol, and wherein said composition is free of conventional neutralizers to achieve gelation, wherein said conventional neutralizers are selected from the group consisting of sodium hydroxide, potassium hydroxide, ammonium hydroxide, aminomethyl propanol, tetrahydroxypropyl ethylenediamine, triethanolamine, tromethamine, PEG-15 cocamine, diisopropanolamine, and triisopropanolamine, wherein said composition is free of buffers, and wherein the admixing step consists of (a) substantially solubilizing the estrogen in the gelation promoter or in an aqueous solution thereof to form a substantially solubilized estrogen preparation and (b) combining the substantially solubilized estrogen preparation with the hydrogen-bonding gelation polymer to form the pharmaceutical composition.

15. A method of vaginal administration of estrogen for a female comprising the step of administering the pharmaceutical composition of claim 1 to the vaginal epithelial tissue of the female.

16. A pharmaceutical composition for vaginal administration consisting of:
(a) 17β-estradiol in an amount of about 0.0005% to about 0.05% by weight of the composition;
(b) at least one hydrogen-bonding gelation polymer that is a homopolymer, copolymer or interpolymer of acrylic acid;
(c) at least one gelation promoter selected from the group consisting of polyhydric alcohols, polyglycols and combinations thereof; and
(d) water, and
wherein the gelation promoter is in an amount effective to gel the polymer and to substantially solubilize the 17β-estradiol so that at least 50% of the 17β-estradiol is dissolved in the composition at 15° C.; and gelling of the polymer is caused by hydrogen-bonding with functional groups of the gelation promoter.

17. The pharmaceutical composition of claim 16, wherein the gelation promoter is polyethylene glycol.

18. The pharmaceutical composition of claim 16, wherein the gelation promoter is propylene glycol.

19. The pharmaceutical composition of claim 16, wherein the gelation promoter is a combination of polyethylene glycol and propylene glycol.

20. The pharmaceutical composition of claim 16, wherein the at least one hydrogen-bonding gelation polymer is present in an amount sufficient to form a gel with a viscosity ranging from about 50 Pa·s to about 1000 Pa·s at 20° C.

21. A pharmaceutical composition for vaginal administration consisting of:
(a) at least one estrogen selected from 17β-estradiol or salt thereof in an amount of about 0.00001% to about 2% by weight of the composition;
(b) at least one hydrogen-bonding gelation polymer that is a homopolymer, copolymer or interpolymer of acrylic acid;
(c) at least one gelation promoter selected from the group consisting of polyhydric alcohols, polyglycols and combinations thereof in an amount effective to gel said polymer and to substantially solubilize the estrogen; and
(d) at least one preservative,
wherein at least 50% of the estrogen is dissolved in said composition at 15° C., and
wherein said composition is substantially free of ethanol.

22. A pharmaceutical composition for vaginal administration consisting of:
(a) at least one estrogen selected from 17β-estradiol or salt thereof in an amount of about 0.00001% to about 2% by weight of the composition;
(b) at least one hydrogen-bonding gelation polymer that is a homopolymer, copolymer or interpolymer of acrylic acid; and
(c) at least one gelation promoter selected from the group consisting of polyhydric alcohols, polyglycols and combinations thereof in an amount effective to gel said polymer and to substantially solubilize the estrogen,
wherein at least 50% of the estrogen is dissolved in said composition at 15° C.,
wherein said composition is substantially free of ethanol,
wherein said composition is free of conventional neutralizers and buffers that increase the pH to achieve gelation, and
wherein said conventional neutralizers are selected from the group consisting of sodium hydroxide, potassium hydroxide, ammonium hydroxide, aminomethyl propanol, tetrahydroxypropyl ethylenediamine, triethanolamine, tromethamine, PEG-15 cocamine, diisopropanolamine, and triisopropanolamine.

* * * * *